US00PP10860P

United States Patent [19]

Bull

[11] Patent Number: Plant 10,860

[45] Date of Patent: Apr. 20, 1999

[54] NEW GUINEA IMPATIENS PLANT NAMED 'LISA'

[76] Inventor: Norbert Bull, Gaertnersiedlung 2, 24610 Goennebek, Germany

[21] Appl. No.: 08/897,986

[22] Filed: Jun. 23, 1997

[51] Int. Cl.[6] ..... A01N 5/00

[52] U.S. Cl. ..... Plt./318

[58] Field of Search ..... Plt./87.6, 318

[56] References Cited

U.S. PATENT DOCUMENTS

P.P. 8,360 8/1993 Bull ..... Plt./87.6

*Primary Examiner*—Howard J. Locker
*Assistant Examiner*—Kent L. Bell
*Attorney, Agent, or Firm*—Foley & Lardner

[57] ABSTRACT

A new and distinct cultivar of New Guinea Impatiens plant named 'Lisa', characterized by its flowers, medium green foliage with yellow variegation on leaves well exposed to light, compact plant habit, and medium flowering response.

1 Drawing Sheet

The present invention comprises a new and distinct cultivar of New Guinea Impatiens, referred to by the cultivar name 'Lisa'.

'Lisa' is a product of a planned breeding program and was originated from a hybridization made by the inventor Norbert Bull in a controlled breeding program in Goennebek, Germany, in 1993. The female parent was a seedling designated no. 24 and the male parent was a seedling designated no. 4. Both parents are proprietary cultivars used in the breeding program.

'Lisa' was discovered and selected as one flowering plant within the progeny of the stated cross by the inventor in 1994 in a controlled environment in Goennebek, Germany.

The first act of vegetative or asexual reproduction of 'Lisa' was accomplished when cuttings were taken from the initial selection in Autumn 1994 in a controlled environment in Goennebek by, or under the supervision of, Norbert Bull.

Horticultural examination of plants grown from these cuttings initiated in Spring 1995 in Goennebek, Germany, and continuing thereafter, has demonstrated that the combination of characteristics as herein disclosed for 'Lisa' are firmly fixed and are retained through successive generations of asexual reproduction.

'Lisa' has not been observed under all possible environmental conditions. The phenotype may vary significantly with variations in environment such as temperature, light intensity and day length, without, however, any variation in genotype.

The following observations, measurement, and comparisons describe plants grown in Hillscheid, Federal Republic of Germany under greenhouse conditions which approximate those generally used in commercial practice.

The following traits have been repeatedly observed and are determined to be basic characteristics of 'Lisa', which in combination distinguish this impatiens as a new and distinct cultivar:

1. Light pink flower color with purple eye
2. Medium sized flowers
3. Medium green foliage, with yellow variegation on leaves that are well exposed to light
4. Compact growth habit
5. Medium flowering response
6. Very resistant to powdery mildew Of the many commercial cultivars known to the present inventor, the most similar in comparison to 'Lisa' is the commercial variety 'Barbara' (unpatented). In comparison to 'Barbara', 'Lisa' has a more compact plant habit, a somewhat more intense, more salmon shade of flower color (R.H.S. 67 D compared to R.H.S. 61 D for 'Barbara'), and a tendency to develop yellow variegated leaves under certain growing conditions, as contrasted to the uniform green foliage of 'Barbara'.

The accompanying colored photographic drawing shows typical flower and foliage characteristics of 'Lisa', with colors being as true as possible with illustrations of this type. In this regard the colors in the illustration appear lighter than the actual R.H.S. values for 'Lisa'. The lighting is bright as to give the appearance of lighter, less-intense hues. The illustration depicts a relatively immature cultivar.

In the following description color references are made to The Royal Horticultural Society Colour Chart.

The color values were determined indoors from flowers taken from plants grown in Hillscheid, Federal Republic of Germany, under greenhouse conditions which approximate those generally used in commercial practice.

The description is based on plants which were planted as rooted cuttings in 10 cm pots in early March and then grown in a greenhouse at 20° C. minimum temperature.

Classification:

*Botanical.*—A hybrid of the genus Impatiens.
*Commercial.*—New Guinea Impatiens cv 'Lisa'.

Plant

A. General appearance and form:

*Habit.*—Relatively compact, low mounded, medium wide, medium vigor, and growth is indeterminate, although weak after flowering begins.
*Height.*—11 cm (10 week old plants).
*Width.*—30 cm.
*Internode length.*—30 mm.
*Stem color.*—Reddish.
*Flowering response.*—8–9 weeks after planting of rooted cuttings.
*Flowering season.*—Generally indeterminate, mainly from March to October, depending on light intensity.
*Lasting quality of the bloom.*—About three weeks.
*Propagation.*—Usually terminal tips for cuttings.
*Rooting.*—Color is R.H.S. 159 B–C; roots initiate in about 18 days at 22° C., from sticking to transplanting; no distinguishing rooting habit.

B. Foliage:

*Shape of leaf.*—Elliptic, with acute base and slightly acuminate apex.
*Margin.*—Slightly serrated, ciliated.
*Leaf, length.*—130 mm.

*Leaf, width.*—Relatively broad, 42–48 mm.

*Main color of upper surface.*—Intense green, 137 A–B.

*Leaf arrangement.*—Primarily in whorls.

*Veins on upper surface, color.*—Pink to light red near the base of the leaf, light green from the base to the tip.

*Variegation on leaf.*—Present on leaves well exposed to the light especially during the summer months; visible along the midrib and the base of lateral veins, width up to half the width of the leaf; color of variegation is greenish yellow, R.H.S. 151 A; variegation is not always visible in immature plants, during spring, or in low-intensity light, as in shaded areas.

*Main color of lower surface.*—Light green, about R.H.S. 138 B with variegation hardly visible.

*Veins on lower surface, color.*—Medium red, about R.H.S. 47 B.

*Petiole, color.*—Reddish, about R.H.S. 47 B.

Inflorescence

A. Flower:

*Flower number per node.*—About 6, in various stages of development, usually one flower per leaf.

*Form of corolla.*—5 petals per flower.

*Shape.*—Almost flat, slightly zygomorph, horizontal, upper petal slightly curved.

*Average length.*—60 mm.

*Average width.*—53 mm.

*Color (general tonality from a distance of three meters)* .—Pink to light pink.

*Petal number.*—Five (5).

*Petal shape.*—Heart-shaped, moderately lobed.

*Petal size.*—Length is about 26 mm and width is about 25 mm.

*Petal texture.*—Smooth.

*Main color of upper surface.*—About R.H.S. 67 D, may later fade to 68 C.

*Color of lower surface.*—R.H.S. 67 D-58 D.

*Eye zone.*—Distinct, red purple, R.H.S. 66 A.

*Spur, color.*—Dark red, about R.H.S. 53 C.

*Spur shape and size.*—Downwardly curved, about 50–55 mm in length.

*Pedicel, color.*—Dark red, about 47 B.

*Petiole, length.*—About 32 mm.

B. Reproductive organs:

*Androecium.*—

Stamens: Five (5) in number, fused, upper surface color is about R.H.S. 57 B.

*Anthers.*—Hooded, color is about R.H.S. 11 D.

*Pollen.*—Color is about R.H.S. 4 D.

*Gynoecium.*—

Stigma and style: Five (5) in number, very short, nearly colorless, about R.H.S. 11 D.

*Ovary.*—Five (5) celled, 5 mm in length, surface color is about R.H.S. 137 B.

I claim:

1. A new and distinct cultivar of New Guinea Impatiens plant named 'Lisa', as illustrated and described.

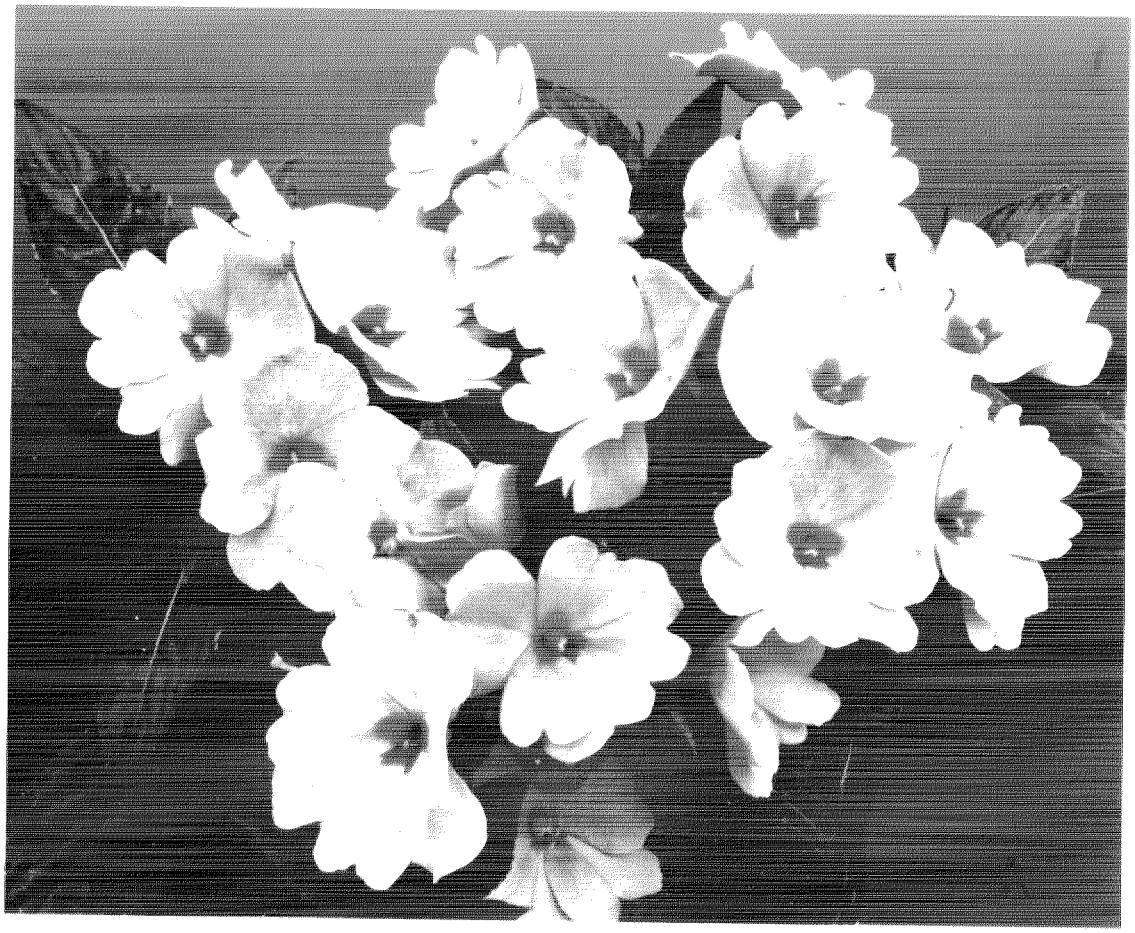

* * * * *